United States Patent
Wojcik

(10) Patent No.: US 10,668,318 B2
(45) Date of Patent: Jun. 2, 2020

(54) COMPLEMENTARY KNEE AND WRIST SUPPORTS

(71) Applicant: Claudia Coe Wojcik, North Kingstown, RI (US)

(72) Inventor: Claudia Coe Wojcik, North Kingstown, RI (US)

(\*) Notice: Subject to any disclaimer, the term of this patent is extended or adjusted under 35 U.S.C. 154(b) by 334 days.

(21) Appl. No.: 15/631,301

(22) Filed: Jun. 23, 2017

(65) Prior Publication Data

US 2017/0368408 A1 Dec. 28, 2017

Related U.S. Application Data

(60) Provisional application No. 62/353,727, filed on Jun. 23, 2016.

(51) Int. Cl.
| | |
|---|---|
| *A63B 21/00* | (2006.01) |
| *A61F 13/10* | (2006.01) |
| *A61F 13/06* | (2006.01) |
| *A47C 16/04* | (2006.01) |

(52) U.S. Cl.
CPC .......... *A63B 21/4039* (2015.10); *A47C 16/04* (2013.01); *A61F 13/061* (2013.01); *A61F 13/107* (2013.01); *A63B 21/4037* (2015.10)

(58) Field of Classification Search
CPC . A63B 21/4039; A63B 21/4037; A47C 16/04; A61F 13/061; A61F 13/107
USPC .............................................. 5/636; D6/601
See application file for complete search history.

(56) References Cited

U.S. PATENT DOCUMENTS

| | | | | |
|---|---|---|---|---|
| 2,448,427 A | \* | 8/1948 | Gordon ................ | A47C 9/027 182/230 |
| 2,940,088 A | \* | 6/1960 | Boos .................... | A47G 9/10 5/636 |
| 3,118,152 A | \* | 1/1964 | Talley, Jr. ............ | A47C 20/025 5/631 |
| 3,287,747 A | \* | 11/1966 | Ellsorth ............... | A47C 20/025 5/631 |
| 3,988,793 A | \* | 11/1976 | Abitbol ................ | A47C 20/025 601/11 |
| 5,237,712 A | \* | 8/1993 | Ramsay ............... | A47C 20/025 5/710 |
| 5,400,449 A | \* | 3/1995 | Satto .................... | A47C 20/021 5/631 |
| 5,781,947 A | \* | 7/1998 | Sramek ................ | A47G 9/10 5/636 |
| 5,848,448 A | \* | 12/1998 | Boyd ................... | A47G 9/10 5/636 |

(Continued)

*Primary Examiner* — Peter M. Cuomo
*Assistant Examiner* — Myles A Throop
(74) *Attorney, Agent, or Firm* — Barlow, Josephs & Holmes, Ltd.

(57) ABSTRACT

An exercise support structure includes a knee support having a tiered recess with a bottom wall, a lower circular tier, and an upper egg-shaped tier; and a wrist support having a tiered support structure with a bottom wall, a lower egg-shaped tier and an upper circular tier, where the knee support and the wrist support are complementary in shape and are interfittingly received in mated relation to form a block. The edges of the tiers may be beveled, forming a smooth transition therebetween. The structure may be made from a soft, durable resilient material, such as foam, silicone gel, rubber, synthetic rubber, or organic tree sap.

8 Claims, 11 Drawing Sheets

(56) References Cited

U.S. PATENT DOCUMENTS

| | | | | |
|---|---|---|---|---|
| 6,233,768 B1* | 5/2001 | Harding | A47C 20/025 | 5/706 |
| 6,536,058 B1* | 3/2003 | Chang | A47G 9/1009 | 5/636 |
| 6,931,684 B1* | 8/2005 | Henegar | A61G 7/02 | 5/604 |
| 9,555,275 B1* | 1/2017 | Izzolo, Jr. | A63B 23/00 | |
| 2003/0019007 A1* | 1/2003 | Spencer | A47C 9/027 | 2/24 |
| 2004/0220018 A1* | 11/2004 | Branson | A63B 21/00047 | 482/51 |
| 2005/0124468 A1* | 6/2005 | Wong | A63B 21/00047 | 482/52 |
| 2005/0189809 A1* | 9/2005 | Lombert | A47C 16/04 | 297/452.26 |
| 2005/0262637 A1* | 12/2005 | Funatogawa | A47G 9/10 | 5/636 |
| 2006/0230538 A1* | 10/2006 | Brown | A47C 16/04 | 5/652 |
| 2009/0247378 A1* | 10/2009 | Carlesimo | A63B 21/00047 | 482/141 |
| 2011/0083278 A1* | 4/2011 | Muratalla | A47G 9/1054 | 5/655.9 |
| 2013/0198953 A1* | 8/2013 | Long | A47G 9/06 | 5/417 |
| 2014/0026323 A1* | 1/2014 | Bowers | A47G 9/10 | 5/636 |
| 2014/0121081 A1* | 5/2014 | Yu | A61F 5/01 | 482/142 |
| 2014/0317851 A1* | 10/2014 | Hammack | A47G 9/10 | 5/640 |
| 2015/0111709 A1* | 4/2015 | Longfellow | A63B 21/068 | 482/140 |
| 2016/0066697 A1* | 3/2016 | Adams | A47G 9/1081 | 5/636 |
| 2018/0263375 A1* | 9/2018 | Stewart | A47C 20/025 | |

\* cited by examiner

US 10,668,318 B2

COMPLEMENTARY KNEE AND WRIST SUPPORTS

CROSS-REFERENCE TO RELATED APPLICATION

This patent document claim priority to earlier filed U.S. Provisional Patent Application No. 62/353,727, filed on Jun. 23, 2016, the entire contents of which are incorporated herein by reference.

BACKGROUND

1. Technical Field

This patent document relates generally to knee supports, and more particularly to complementary knee and wrists support configured to protect the knees and wrists while exercising or during other physical or leisure activities.

2. Background of the Related Art

Persons that have degenerative knee conditions and/or have had knee injuries and/or knee surgery can suffer from significant pain when kneeling. This pain causes frustration and discourages those persons from engaging in activities, such as yoga, that may require kneeling. Additionally, exercises, such as yoga, gardening, leisure, etc., also place stress on the wrists and arms, and persons that have wrist and/or arm conditions, such as carpal tunnel are also affected by pain while exercising. Therefore, there is a perceived need for a device configured to aid and promote proper support for a person's knees and wrists, thereby reducing the stresses and pain on the person's knees and wrists and allowing the person to engage in activities that may require prolonged kneeling or postural support relative to the ground.

SUMMARY

The knee and wrist support disclosed herein solves the problems of the prior art by providing a knee support that cups and supports a person's knee while kneeling and complimentary wrist support that supports a person's hand.

The knee support includes a body with a knee cavity formed therein. The body may be unitarily formed or formed from a layered structure. The cavity may include a egg-shaped cutout to cup the knee. The edges of the egg-shaped cutout may be beveled. The knee support may be formed from a resilient material, such a foam, but is not limited thereto.

Because the person's knee is supported from the larger bone structures, the present knee support reduces stresses on the knee and consequently pain experienced by the user. This permits the user to engage in physical and leisure activities that may require kneeling, such as yoga, gardening and the like. Furthermore, because a person may now engage in an activity such as yoga, this permits the person to stretch tight ligaments, thereby improving a person's range of motion and generally relieving stress in the joint, which strengthen and lengthen.

The wrist support is a complementary shape to the knee support. A cushioned layer forms a bottom of the wrist/hand support. Attached to the base and proximate the center of the base layer, is a generally egg-shaped, second layer to support a person's wrist. Attached to the egg-shaped layer is a generally circular or oblong third layer positioned proximate the wider end of the egg-shaped layer forming a support for the palm of a person's hand. The second and third layers of the hand support together form a support for the hand of a user.

The size and dimensions of the wrist support and the positioning of the support structures on the hand support are reciprocal and complimentary to the knee cavity and body of the knee support. Consequently, the hand support may be interfit with the knee support by inserting the support into the knee cavity and pressing them together. The hand support and knee support are held together via the frictional engagement of the foam. When coupled together, the knee support and hand support form a cuboid, or substantially rectangular box or brick shaped structure, which may conveniently be used as a yoga block.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENT

Figure 1:
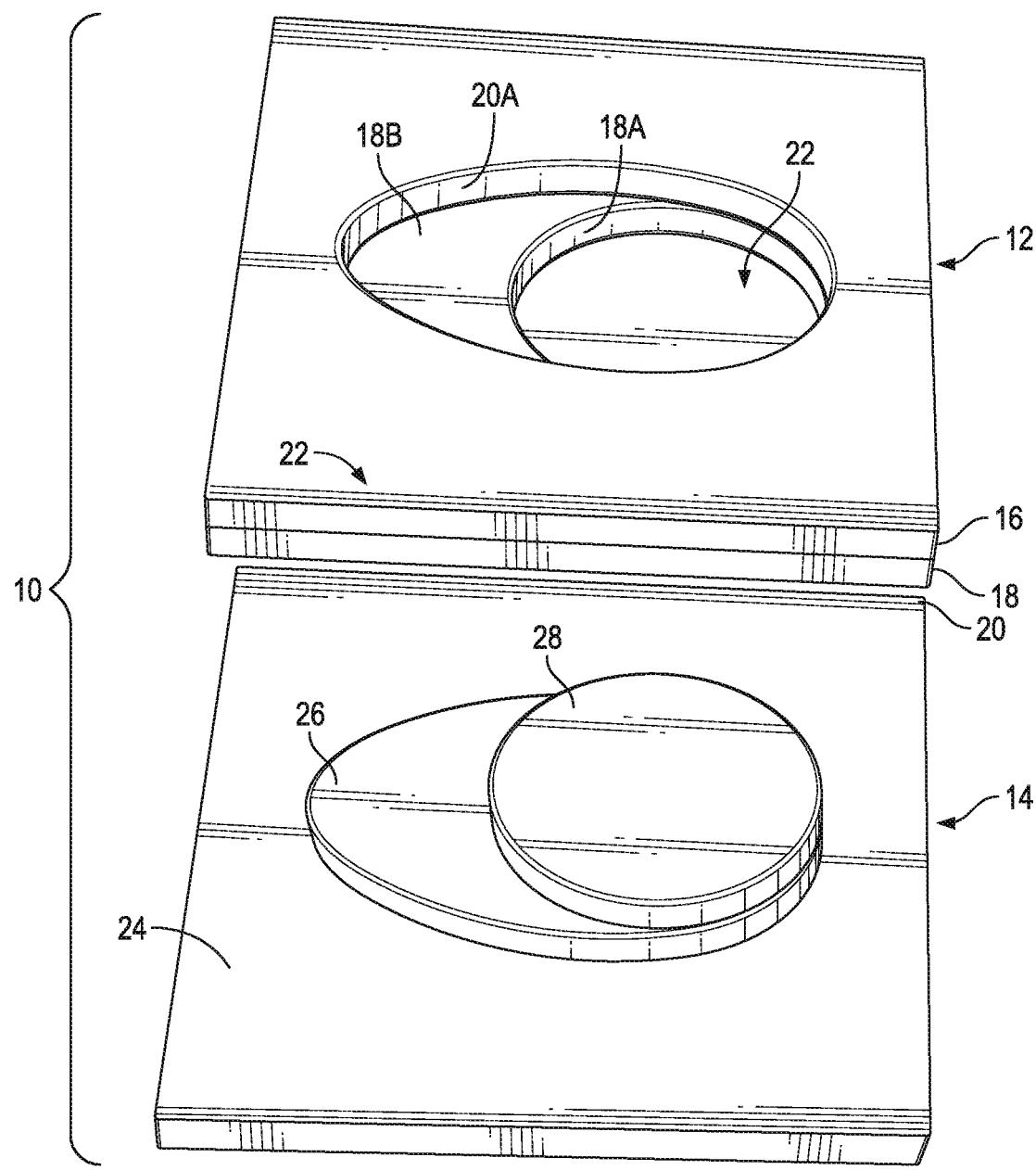
FIG. 1 shows a top, rear perspective view of an exemplary embodiment of a complimentary knee and wrist support.
Figure 2:
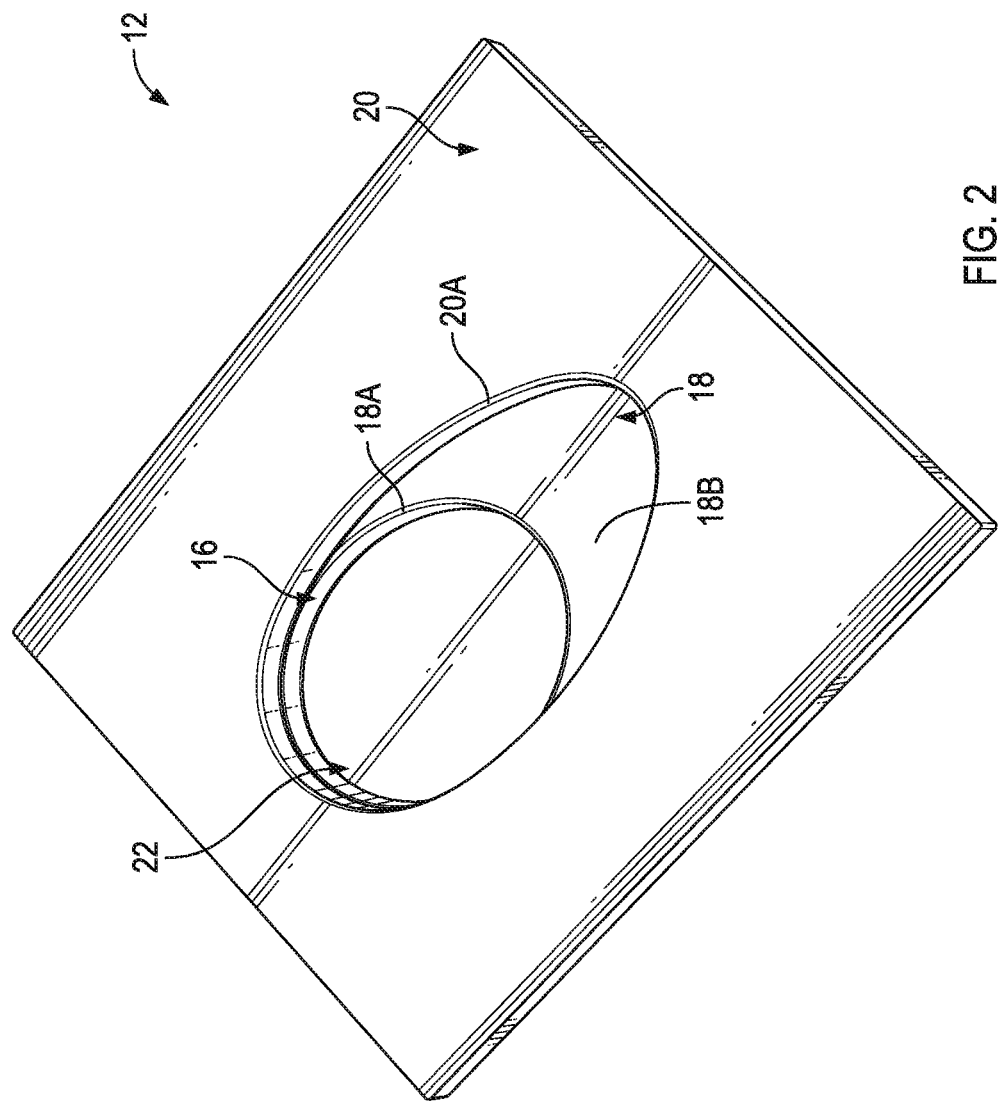
FIG. 2 shows a top perspective view of an exemplary embodiment of a knee support.
Figure 3:
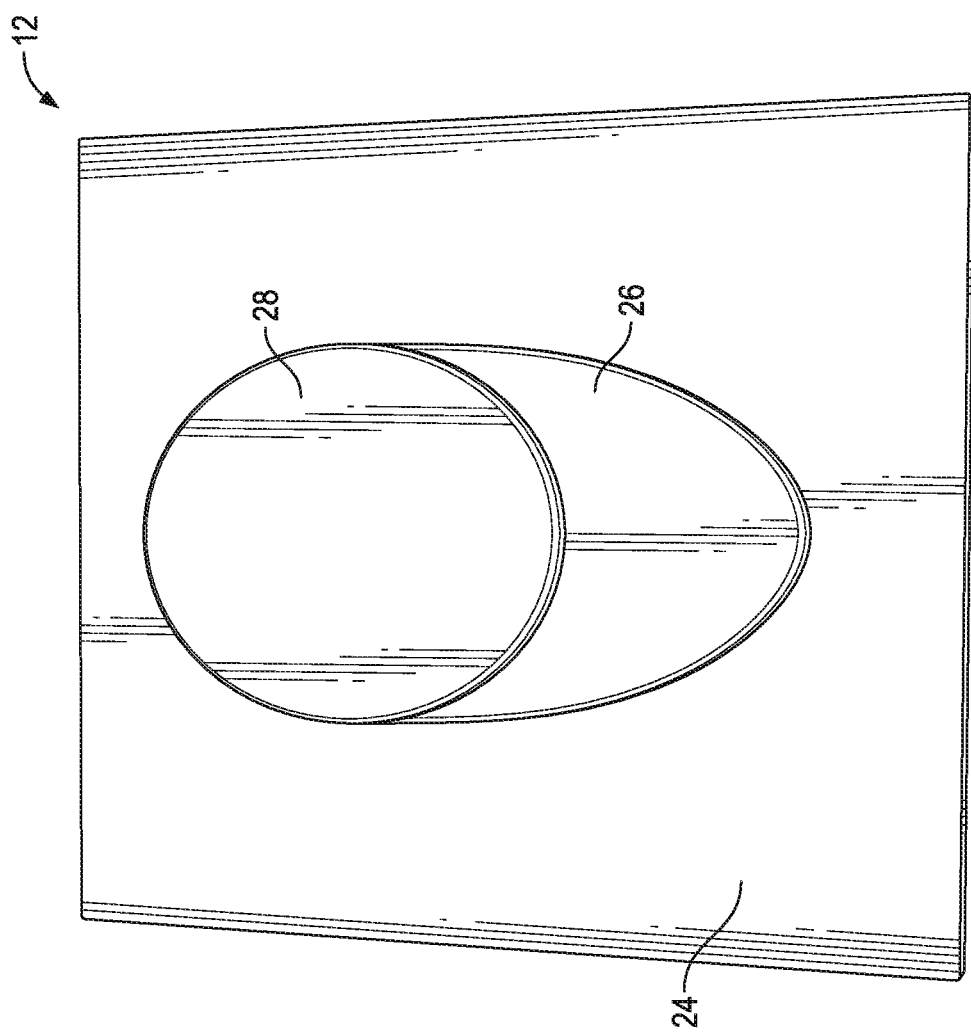
FIG. 3 shows a top, front perspective view of an exemplary embodiment of a wrist support.
Figure 4:
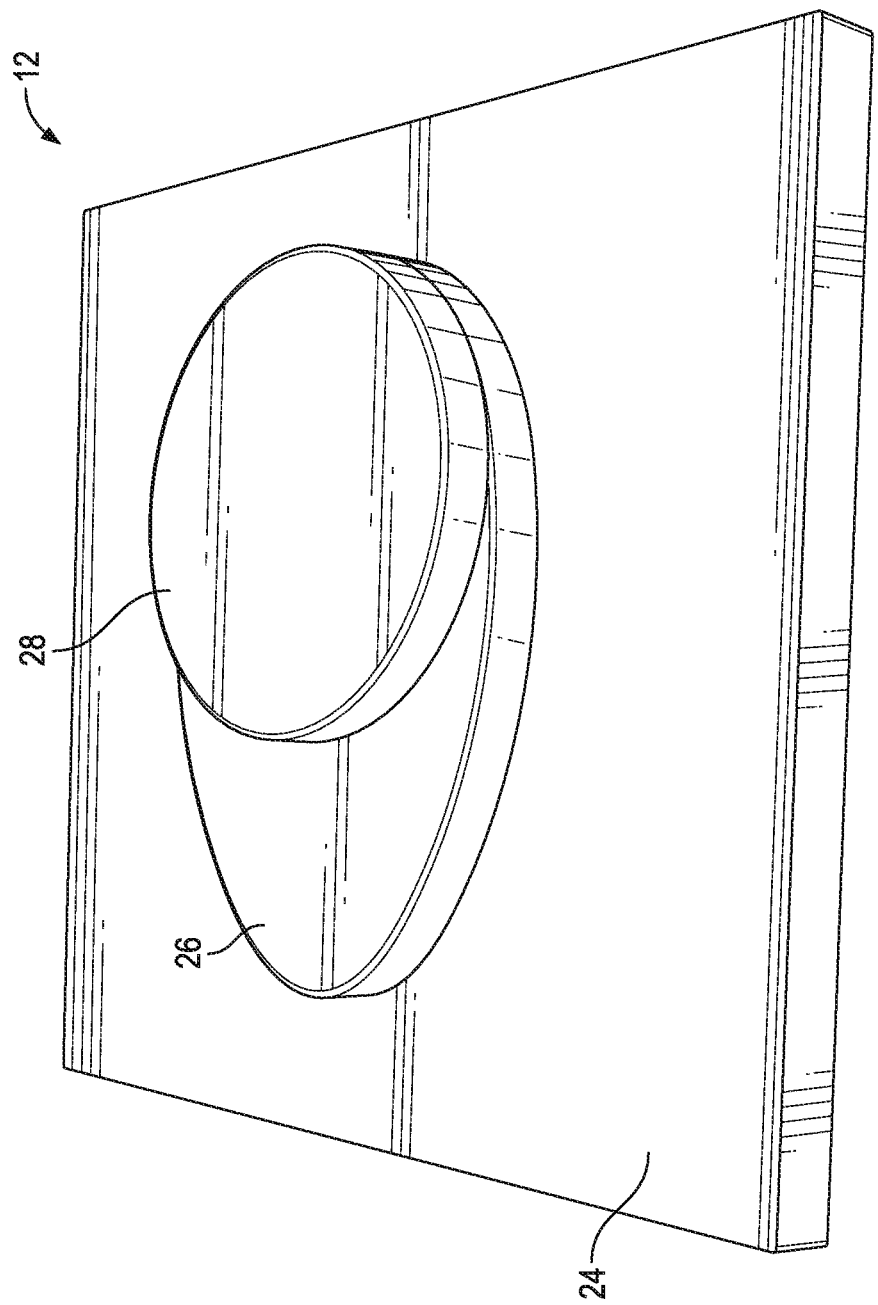
FIG. 4 shows a top, right side perspective view of an exemplary embodiment of a wrist support.

Referring now to FIG. 1, an exemplary embodiment of the knee support with complimentary wrist/hand support are shown in a disassembled or separated state, generally at 10. The support 10 includes a knee support 12 and a wrist support 14 that complimentarily fit or interfit together. Each portion of the knee and wrist support 10 generally includes a body having top, bottom, front, rear and left and right sides. The body may be formed from a soft, durable, resilient material, such as foam, silicone gel, rubber, or organic tree sap. The foam may be open cell foam or closed cell foam as desired. Suitable foams may be formed from polyurethane, polystyrene, polybutadiene and copolymers thereof. Other synthetic rubbers and polymers may be used as well. In one exemplary embodiment, the knee and wrist support may be constructed of high-density cross-linked polyethylene foam.

Figure 9:
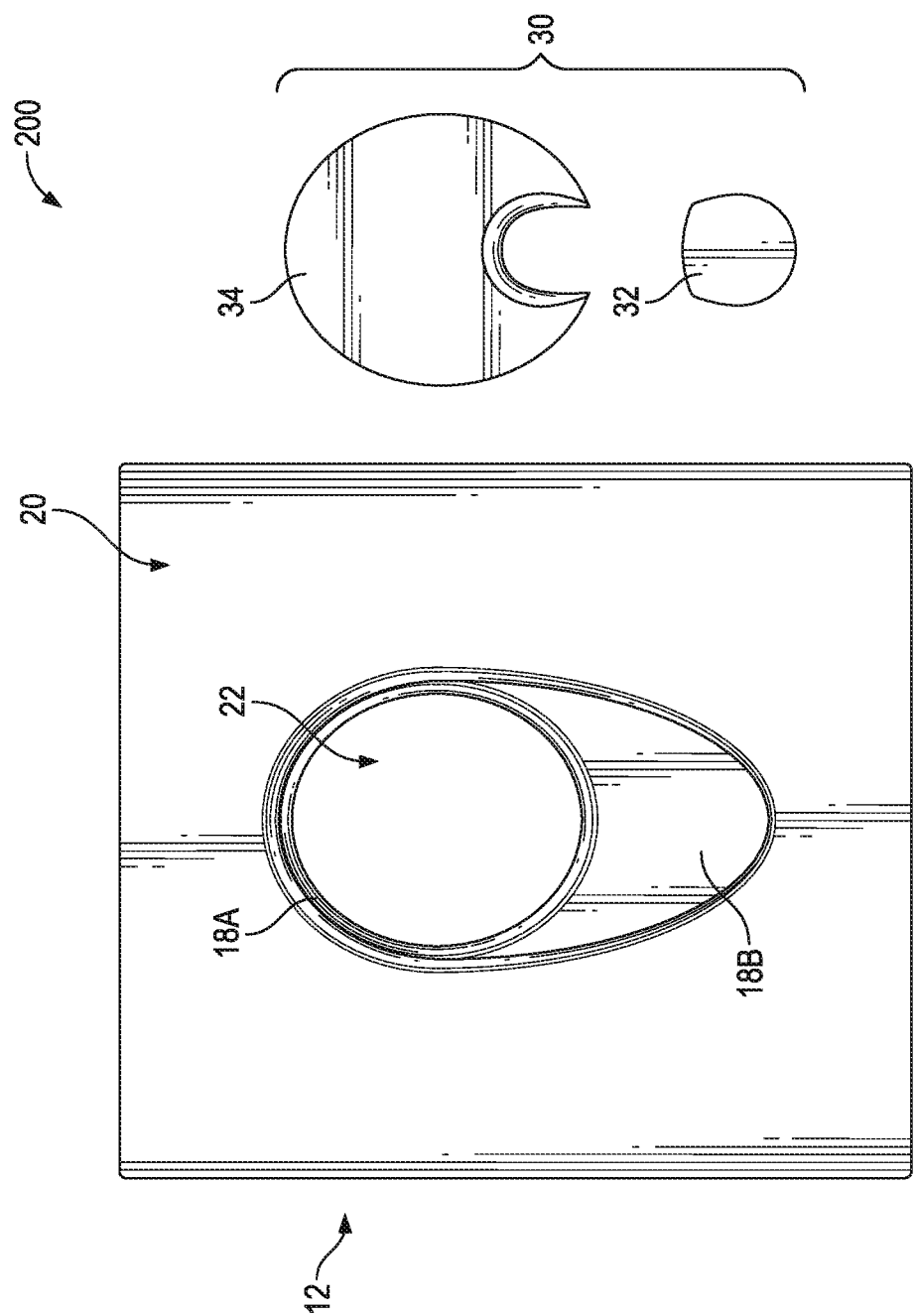
FIG. 9 shows a top view of an alternative embodiment of a knee support and a segmented insert fin a disassembled state.

The knee support 12 may be formed from a number of layers adhered together or alternatively unitarily formed (molded) (best seen in FIG. 9).

In the exemplary embodiment of a knee support 12, the body is formed from a number of layers. A first, or base, layer forms 16 a bottom of the body. A second, or middle, layer 18 is attached to the first layer, adding bulk to the knee support. A generally circular or oblong lower cutout 18A is formed proximate the center of the second layer 18, forming an indentation for a knee cap of a person to rest in. A third, or top, layer 20 is attached to the second layer 18. A generally egg-shaped, upper cutout 20A is formed proximate the center of the top layer 20 and configured to align with a portion of the cutout 18A on the second layer 18, exposing a portion of the second layer 18 and forming a shelf 18B for a person's upper shin, specifically the tibia, to rest against. The upper and lower cutouts 18A, 20A together form a knee cavity 22 in the body of the knee support 12. The edges on the cutouts 18A, 20A may be beveled, forming a gradual transition between the layers 16, 18, 20.

The knee cavity 22 formed in the body of the knee support 12 allows the tibia bone to rest, further allowing the person's knee muscles and associated ligaments to relax. Specifically, the Medial Collateral Ligament (MCL), the Lateral Collateral Ligament (LCL) are all supported, with the effect of allowing the patella to relax as well. The Anterior Crucial Ligament (ACL) and Posterior Cruciate Ligament (PCL) also find space to slacken and release safely, while safely engaging and supporting the Lateral Meniscus.

The knee support 12 further creates a support system in the person's femur. When the joint is safely supported with gentle compression, bone density is encouraged. Further, the knee support allows synovial fluid freedom to cleanse and flow from and through the knee joint, thereby releasing any particles that may be stuck or stagnant in the knee joint.

In addition to the knee support 12, a complimentary shaped wrist/hand support 14 is provided. Like the knee support 12, the wrist support 14 may be formed from a soft, durable, resilient material, such as polymer foam. The foam may be an open cell foam or a closed cell foam as desired. Suitable foams may be formed from polyurethane, polyethylene and copolymers thereof. Other synthetic rubbers and polymers may be used as well. In an exemplary embodiment, the wrist support 14 may be constructed of a high-density cross-linked polyethylene foam. The wrist support 14 may be formed from a number of layers adhered together, as the knee support described above, or unitarily formed (best seen in FIG. 9).

In an exemplary embodiment, the wrist support is formed from a number of layers. A first, or base, layer 24 forms a bottom of the hand support. Attached to the base and proximate the center of the base layer 24, is a generally egg-shaped, second layer 26 to support a person's wrist. Attached to the egg-shaped layer 26 is a generally circular or oblong third layer 28 positioned proximate the wider end of the egg-shaped layer 26 forming a support for the palm of a person's hand and wrist. The second and third layers 26, 28 of the wrist support 14 together form a support for the hand and wrist of a user. The unique shape of the wrist/hand support 14 provides support for the user's wrists and forearms and relieves stresses on the wrist bones and wrist joint. The edges on the layers 26, 28 may be beveled, forming a gradual transition between the layers 24, 26, 28.

Figure 5:
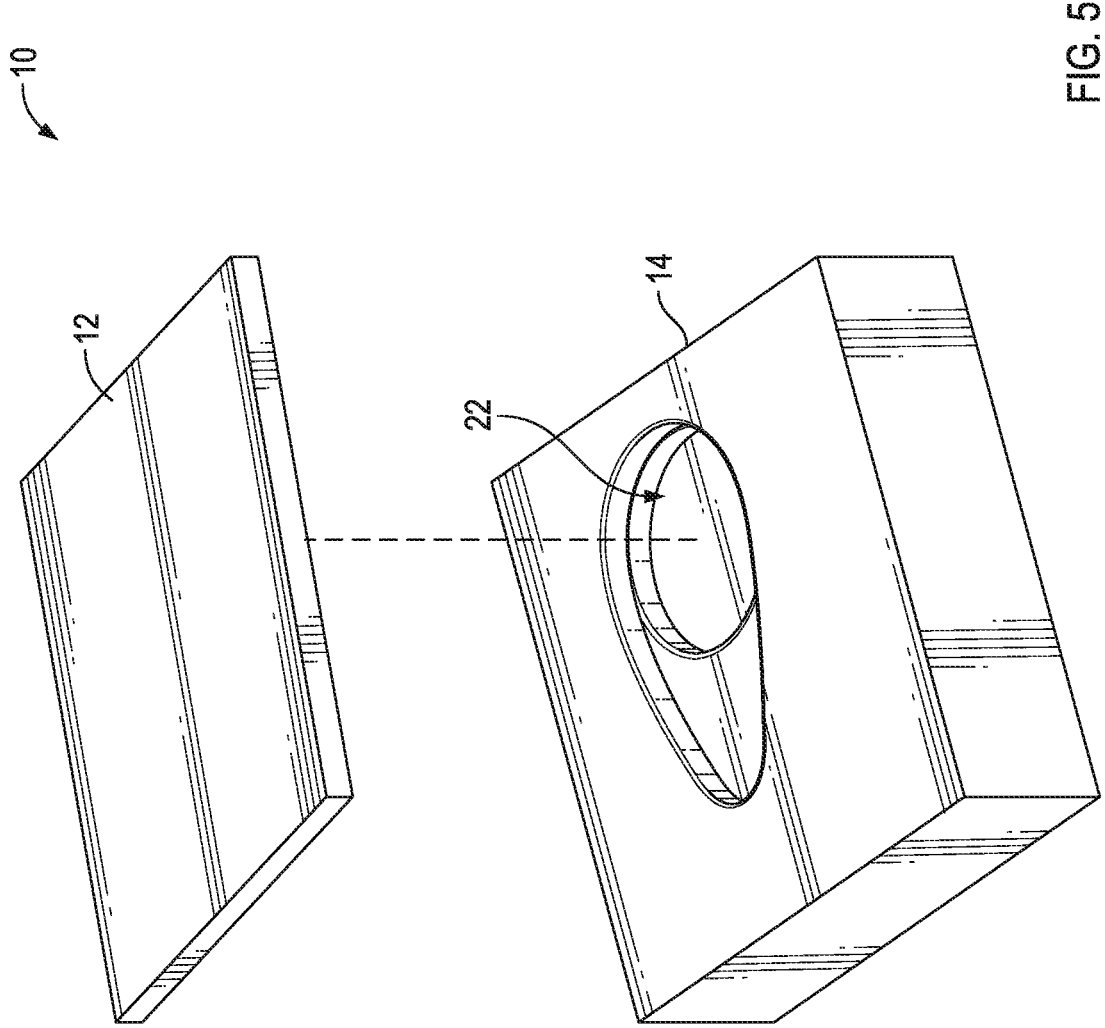
FIG. 5 shows an exploded view of an exemplary embodiment of a complimentary knee and wrist support.
Figure 6:
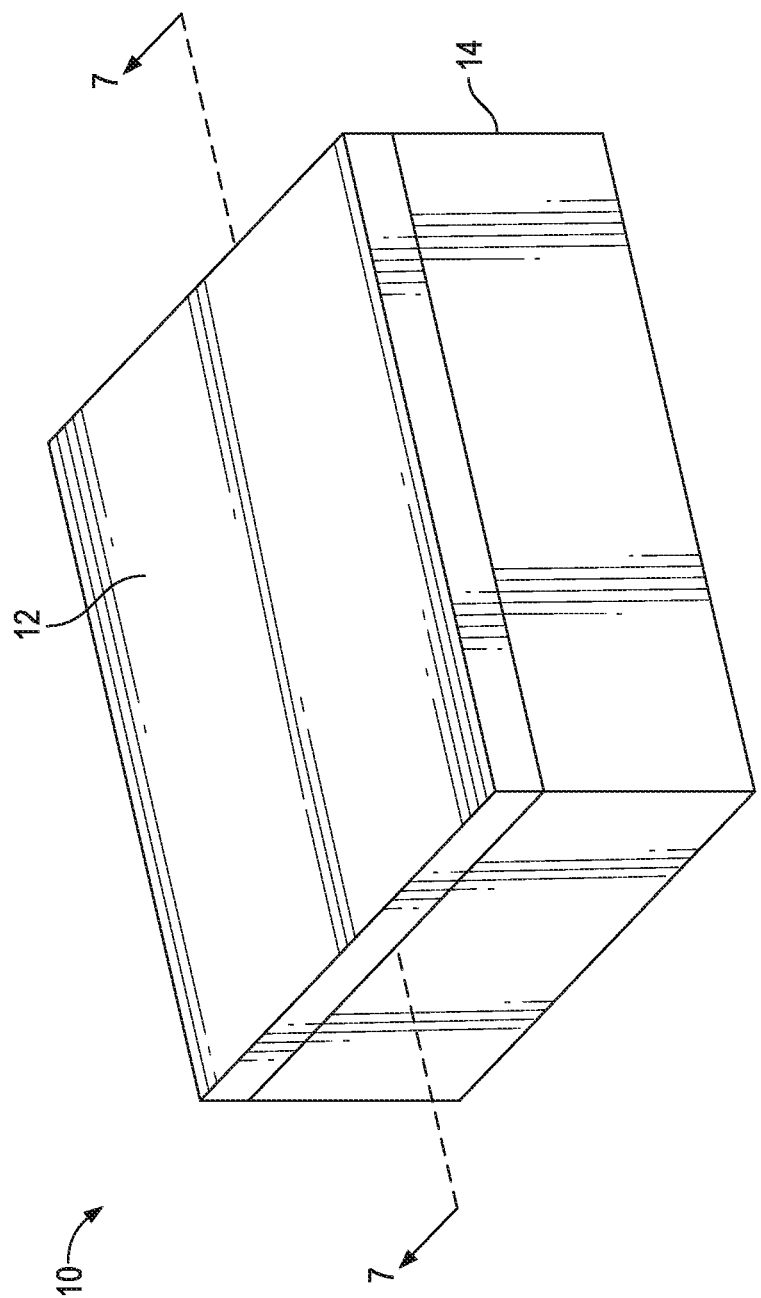
FIG. 6 shows a perspective view of exemplary embodiment of a complimentary knee and wrist support in an assembled relation.
Figure 7:
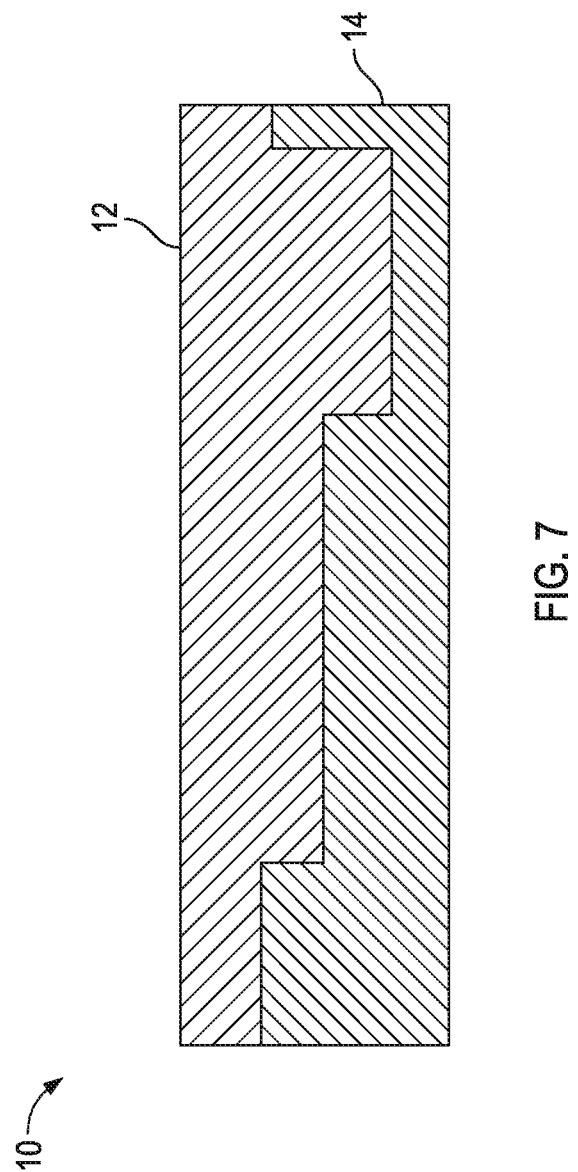
FIG. 7 shows a cross-section view through line 7-7 of FIG. 6.

It is important to note that the size and dimensions of the wrist support layer structures 26, 28 and the positioning of the support structures 26, 28 on the wrist support 14 are reciprocal and complimentary to the knee cavity 22 and body of the knee support 12. Consequently, as illustrated in FIGS. 5-7, the wrist support 14 may be interfit with the knee support 12 by inserting the wrist support 14 into the knee cavity 22 and pressing them together. The wrist support 14 and knee support 12 may held together via the frictional engagement of the foam. When coupled together, the knee support 12 and wrist support 14 form a cuboid, or substantially rectangular box or brick shaped structure, which may conveniently be used as a yoga block (best seen in FIG. 6).

Figure 8:
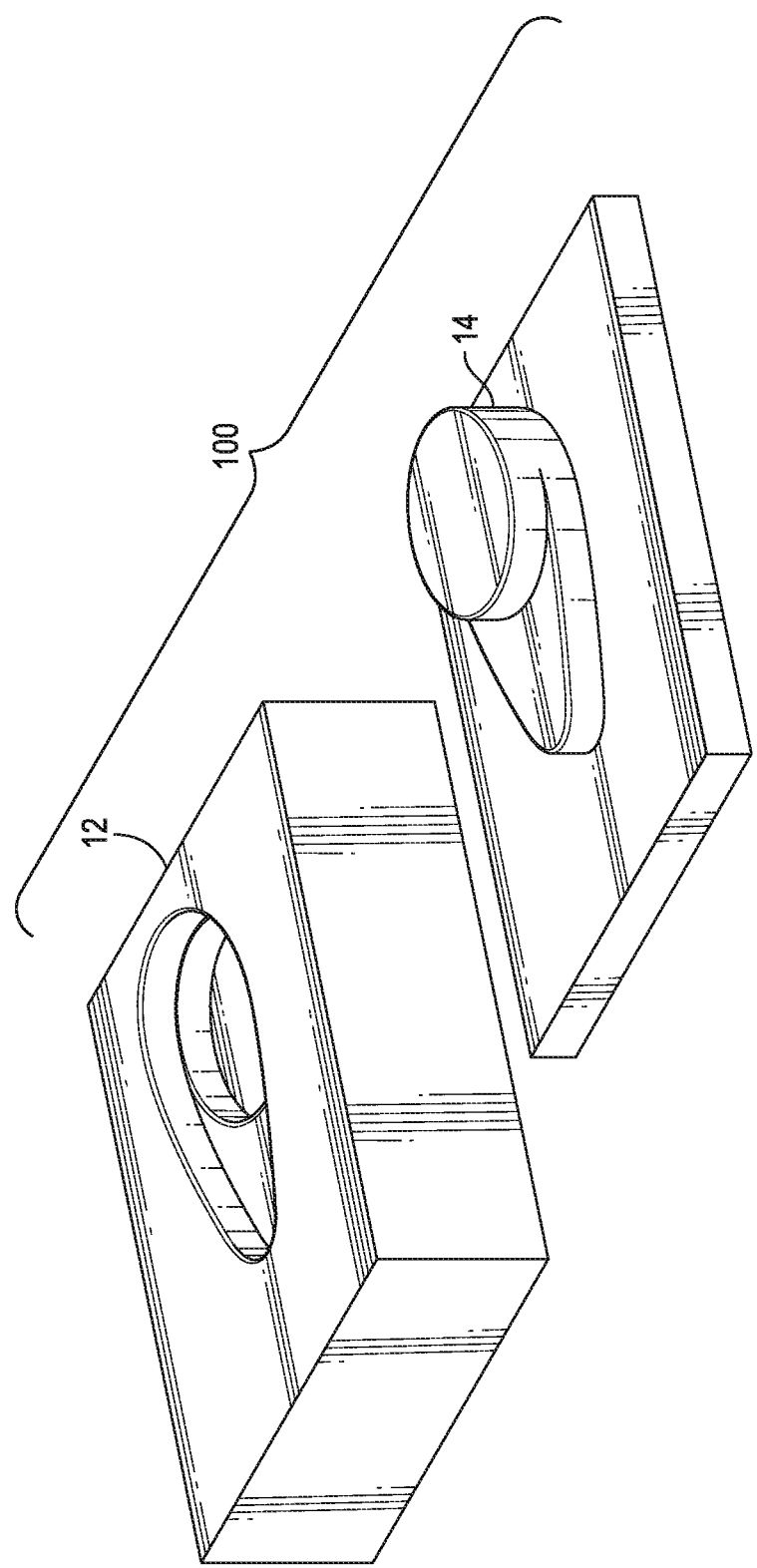
FIG. 8 shows a perspective view of an alternative exemplary embodiment of a complimentary knee and wrist support in a separated state.

Referring to FIG. 8, an alternative embodiment of the complimentary knee and wrist support is shown in a disassembled or separated stated, generally at 100. In this exemplary embodiment, the knee support 12 and wrist support 14 are integrally or unitarily formed (or molded). The alternative embodiment 100 is otherwise the same in all respects as the embodiment 10, described above.

Figure 10:
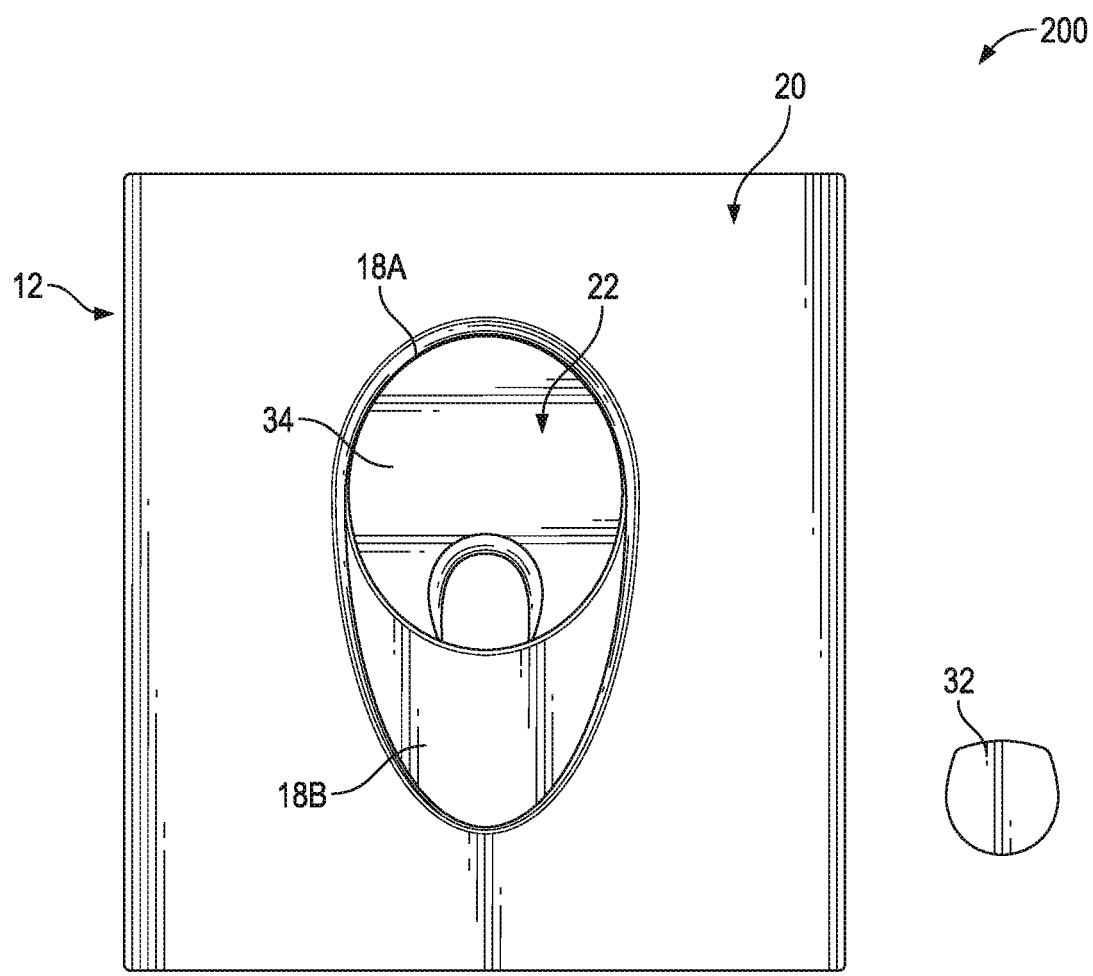
FIG. 10 shows a top view of an alternative embodiment of a knee support and a segmented insert, with a first portion of the segmented insert inserted therein and second portion removed.
Figure 11:
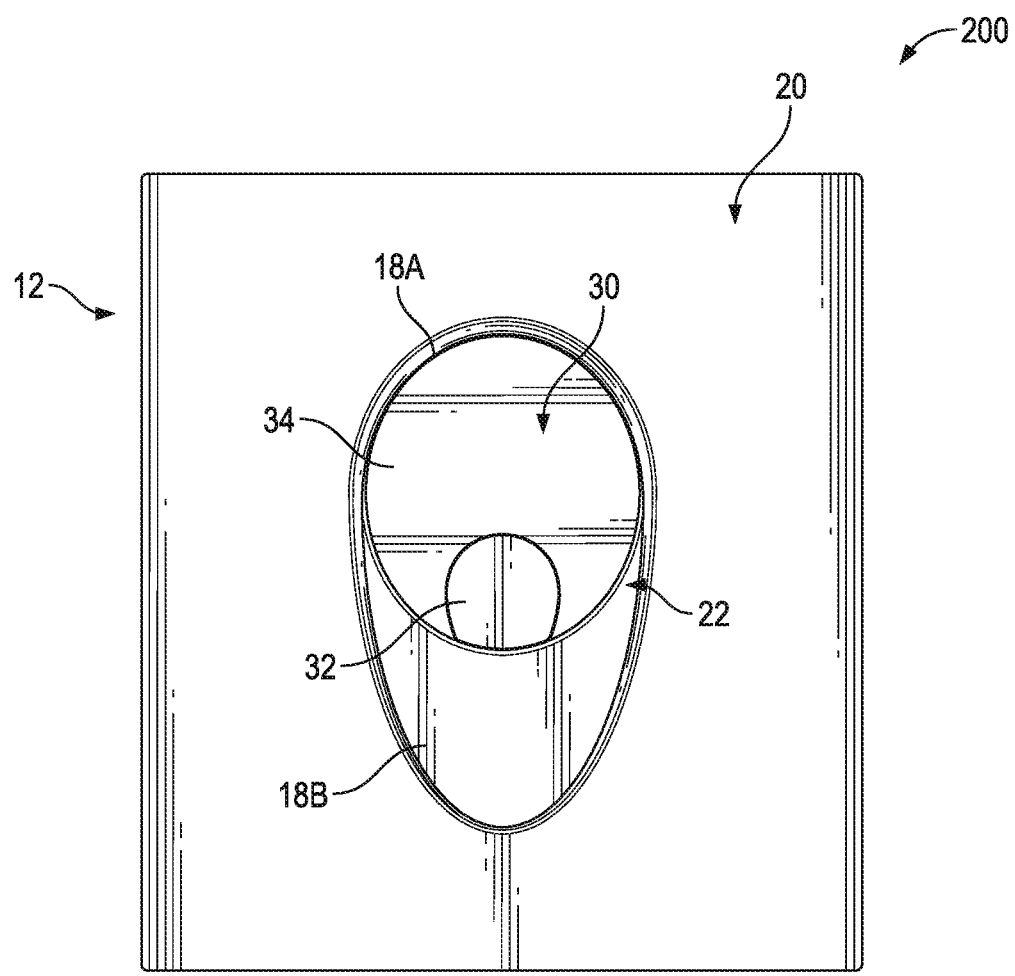
FIG. 11 shows a top view of an alternative embodiment of a knee support with a segmented insert fitted therein.

Referring to FIGS. 9-11, a support element 30 for a knee support 12 is generally illustrated at 200. In this exemplary embodiment 200, the knee support 12 includes a support element 30 sized and dimensioned to fit into the cutout 18A of the knee cavity 22, to provide additional support to a user's knee. The support element 30 may be segmented into multiple, removable elements. For instance, the support element 30 may include a first portion 32 and a second portion 34. The first portion 32 may be circular or semicircular in shape. Removal of the first portion 32, allows ligaments in the knee to also find space to slacken and release safely, while safely engaging and supporting the lateral meniscus. Further, synovial fluid has more freedom to cleanse and flow from and through the knee joint.

It would be appreciated by those skilled in the art that various changes and modifications can be made to the illustrated embodiments without departing from the spirit of the present invention. All such modifications and changes are intended to be within the scope of the present invention.

What is claimed is:

1. A yoga block comprising:
   a knee support having a top side and a bottom side, said top side having a tiered recess extending into the knee support, said tiered recess having a bottom wall and a lower circular tier cutout cooperating with the bottom wall to form an indentation capable of engaging and supporting a knee cap of a user, and said tiered recess further having an upper egg-shaped tier cutout, said egg-shaped tier cutout exposing a shelf adjacent said indentation, said shelf and said top side of said knee support cooperating to receive and support a shin of said user when said knee cap is positioned in said indentation; and
   a wrist support having a top side and a bottom side, said bottom side having a tiered support structure extending outwardly from the wrist support, said tiered support structure having a lower egg-shaped tier layer forming a support shaped for engaging a wrist of said user, and said tiered support structure further having an upper circular tier layer forming a support shaped for engaging a palm of said user,
   wherein the tiered recess of the knee support and the tiered support structure of the wrist support are complementary in shape and are interfittingly received in mated relation such that the knee support and the wrist support cooperate to form a yoga block.

2. The yoga block of claim 1, wherein the knee support and the wrist support each comprise a plurality of foam layers.

3. The yoga block of claim 1, wherein the knee support and the wrist support are unitarily molded of foam.

4. The yoga block of claim 1, wherein the circular tier cutout and upper egg-shaped tier cutout of the knee support have beveled edges, forming a gradual transition therebetween.

5. The yoga block of claim 4, wherein the circular tier layer and the upper egg-shaped tier layer of the wrist support have beveled edges, forming a gradual transition.

6. The yoga block of claim 1, wherein the circular tier layer and the upper egg-shaped tier layer of the wrist support have beveled edges, forming a gradual transition.

7. The yoga block of claim 1, wherein the tiered recess of the knee support and the tiered support structure of the wrist support are frictionally received in mated relation.

8. The yoga block of claim 5, wherein the tiered recess of the knee support and the tiered support structure of the wrist support are frictionally received in mated relation.

\* \* \* \* \*